United States Patent [19]
Young et al.

[11] Patent Number: 5,589,511
[45] Date of Patent: Dec. 31, 1996

[54] METHOD FOR TREATING MIGRAINE HEADACHES USING OPTICALLY PURE S(+) FLUOXETINE

[75] Inventors: James W. Young, Palo Alto, Calif.; Timothy J. Barberich, Concord, Mass.

[73] Assignee: Sepracor Inc., Marlborough, Mass.

[21] Appl. No.: 228,240

[22] Filed: Apr. 15, 1994

Related U.S. Application Data

[63] Continuation-in-part of Ser. No. 67,380, May 26, 1993, abandoned, and Ser. No. 793,036, Nov. 15, 1991, abandoned, which is a continuation-in-part of Ser. No. 566,655, Aug. 13, 1990, Pat. No. 5,104,899, said Ser. No. 67,380, is a division of Ser. No. 793,036.

[51] Int. Cl.$^6$ .................................................. A61K 31/135
[52] U.S. Cl. ........................... 514/646; 514/649; 514/651
[58] Field of Search .................................... 514/646, 649, 514/651

[56] References Cited

U.S. PATENT DOCUMENTS

| | | | |
|---|---|---|---|
| 3,536,809 | 10/1970 | Applezweig | 424/28 |
| 3,598,123 | 8/1971 | Zaffaroni | 128/268 |
| 3,630,200 | 12/1971 | Higuchi | 128/260 |
| 3,845,770 | 11/1974 | Theeuwes et al. | 128/260 |
| 3,916,899 | 11/1975 | Theeuwes et al. | 128/260 |
| 4,008,719 | 2/1977 | Theeuwes et al. | 128/260 |
| 4,018,895 | 4/1977 | Molloy et al. | 424/330 |
| 4,194,009 | 3/1980 | Molloy et al. | 424/330 |
| 4,313,896 | 2/1982 | Molloy et al. | 260/501.18 |
| 4,314,081 | 2/1982 | Molloy et al. | 564/347 |
| 4,329,356 | 5/1982 | Holland | 424/274 |
| 4,444,778 | 4/1984 | Coughlin | 424/262 |
| 4,590,213 | 5/1986 | Stark | 514/653 |
| 4,594,358 | 6/1986 | Hynes | 514/651 |
| 4,596,807 | 6/1986 | Crosby | 514/277 |
| 4,626,549 | 12/1986 | Molloy et al. | 514/651 |
| 4,647,591 | 3/1987 | Cherkin et al. | 514/651 |
| 4,698,342 | 10/1987 | Crosby | 514/253 |
| 4,777,173 | 10/1988 | Shrotryia et al. | 514/252 |
| 4,797,286 | 1/1989 | Thakkar et al. | 424/456 |
| 4,847,092 | 7/1989 | Thakkar et al. | 424/456 |
| 4,868,344 | 9/1989 | Brown | 568/812 |
| 4,895,845 | 1/1990 | Seed | 514/252 |
| 4,918,207 | 4/1990 | Brown | 549/504 |
| 4,918,242 | 4/1990 | Brown | 568/658 |
| 4,918,246 | 4/1990 | Brown | 568/812 |
| 5,114,976 | 5/1992 | Norden | 514/646 |
| 5,250,571 | 10/1993 | Fuller et al. | 514/651 |
| 5,356,934 | 10/1994 | Robertson et al. | 514/649 |

FOREIGN PATENT DOCUMENTS

| | | |
|---|---|---|
| 0294028A2 | 12/1988 | European Pat. Off. . |
| 0369685A1 | 5/1990 | European Pat. Off. . |
| 0449562A2 | 10/1991 | European Pat. Off. . |
| 0449561A2 | 10/1991 | European Pat. Off. . |
| WO89/03692 | 5/1989 | WIPO . |
| 9200103 | 1/1992 | WIPO . |

OTHER PUBLICATIONS

Caccia et al., "Influence of Dose and Route of Administration on the Kinetics of Fluoxetine and Its Metabolite Norfluoxetine in the Rat", *Psychopharmacology*, 100: 509–514 (1990).

Teicher et al., "Emergence of Intense Suicidal Preoccupation During Fluoxetine Treatment", *Am. J. Psychiatry*, 147(2): 207–210 (1990).

Wong et al., "Fluoxetine and Its Two Enantiomers as Selective Serotonin Uptake Inhibitors", *Acta Pharm. Nord.*, 2(3): 171–180 (1990).

Corey and Reichard, "Enantioselective and Practical Syntheses of R–and S–Fluoxetines", *Tetrahedron Lett.*, 30(39): 5207–5210 (1989).

Coutts and Baker, "Implications of Chirality and Geometric Isomerism in Some Psychoactive Drugs and Their Metabolites", *Chirality*, 1:99–120 (1989).

Coutts and Baker, "Metabolic Implications of Chiral Centres in Psychotropic Drugs", *Prog. Neuro–Psychopharmacol. & Biol. Psychiat.*, 13: 405–417 (1989).

Jamali et al., "Enantioselective Aspects of Drug Action and Disposition: Therapeutic Pitfalls", *J. Pharm. Sci.* 78(9): 695–715 (1989).

Gao and Sharpless, "Asymmetric Synthesis of both Enantiomers of Tomoxetine and Fluoxetine. Selective Reduction of 2,3–Epoxycinnamyl Alcohol with Red–Al", *J. Org. Chem.*, 53(17): 4081–4084 (1988).

Kim and Wurtman, "Selective Effects of CGS 10686B, d1–Fenfluramine or Fluoxetine on Nutrient Selection", *Physiology & Behavior*, 42: 319–322 (1988).

Robertson et al., "Absolute Configurations and Pharmacological Activities of the Optical Isomers of Fluoxetine, a Selective Serotonin–Uptake Inhibitor", *J. Med. Chem.*, 31: 1412–1417 (1988).

Wong et al., "Suppression of Food Intake in Rats by Fluoxetine: Comparison of Enantiomers and Effects of Serotonin Antagonists", *Pharmacology Biochemistry & Behavior*, 31: 475–479 (1988).

Benfield et al., "Fluoxetine: A Review of Its Pharmacodynamic and Pharmacokinetic Properties, and Therapeutic Efficacy in Depressive Illness", *Drugs* 32: 481–508 (1986).

Fuller and Snoddy, "Fluoxetine Enantiomers as Antagonists of p–Chloroamphetamine Effects in Rats", *Pharmacology Biochemistry & Behavior*, 24: 281–284 (1986).

(List continued on next page.)

*Primary Examiner*—Kevin E. Weddington
*Attorney, Agent, or Firm*—Pennie & Edmonds

[57] ABSTRACT

Methods and compositions are disclosed utilizing the pure S(+) isomer of fluoxetine which is a potent antidepressant and appetite suppressant substantially free of unwanted, adverse toxic or psychological effects. In addition, methods and compositions are disclosed utilizing the pure S(+) isomer of fluoxetine which is useful in treating migraine headaches, pain, in particular chronic pain, obsessive-compulsive disorders, sexual dysfunction and memory disorders. Further, methods and compositions for treating a condition alleviated or improved by inhibition of serotonin uptake in serotonergic neurons and platelets in a human using optically pure S(+) fluoxetine are disclosed.

10 Claims, No Drawings

OTHER PUBLICATIONS

Scrip's New Product Review, No. 7, pp. 13–14 (1986).

Wong et al., "Inhibition of Serotonin Uptake by Optical Isomers of Fluoxetine", *Drug Development Research*, 6: 397–403 (1985).

Chem Abstract 112 216327E (1990).

Bremner, "Fluoxetine in Depressed Patients: A Comparison with Imipramine", *J. Clin. Psychiatry*, 45(10): 414–420 (1984).

Power–Smith, "Beneficial Sexual Side–effects from Fluoxetine," *Brit. J. Psychiatry* 164: 249–250 (1994).

Saper et al., "Double–Blind Trial of Fluoxetine: Chronic Daily Headache and Migraine," *Headache* 34: 497–502 (1994).

Stevens et al., "Interaction of the Enantiomers of Fluoxetine and Norfluoxetine with Human Liver Cytochromes P450," *J. Pharmacology & Experimental Therapeutics* 226(7): 964–971 (1993).

Adly et al., "Fluoxetine Prophylaxis of Migraine," *Headache* 32: 101–104 (1992).

Bergstrom et al., "Quantification and Mechanism of the Fluoxetine and Tricyclic Antidepressant Interaction," *Clin. Pharmacol. Ther.* 51: 239–248 (1992).

Physicians Desk Reference, pp. 905–908, 44th Ed., Medical Economics Data Production Co., N.J. (1990).

Roberston et al. J. Med. Chem 1988. 31, 1412–1417.

Wong et al. Acta Pharm. Nord. 2(3) 1990. pp. 171–180.

METHOD FOR TREATING MIGRAINE HEADACHES USING OPTICALLY PURE S(+) FLUOXETINE

This is a continuation-in-part of application Ser. No. 07/793,036, filed Nov. 15, 1991, now abandoned, which is a continuation-in-part of application Ser. No. 07/566,655, filed Aug. 13, 1990, now U.S. Pat. No. 5,104,899. This application is also a continuation-in-part of application Ser. No. 08/067,380, filed May 26, 1993 now abandoned, which is a divisional of application Ser. No. 07/793,036, filed Nov. 15, 1991, now abandoned, which is a continuation-in-part of Ser. No. 07/566,655, filed Aug. 13, 1990, now U.S. Pat. No. 5,104,899.

BACKGROUND OF THE INVENTION

This invention relates to a novel composition of matter which possesses potent antidepressant activity as a serotonin uptake inhibitor while avoiding the usual detrimental factors, unwanted effects and adverse toxic or psychological effects associated with such agents. Also disclosed are methods of using said composition to treat depression while avoiding the usual detrimental factors, unwanted effects and side effects associated with such agents.

The invention further relates to a novel composition of matter containing optically pure S(+) fluoxetine which has activity as a weight loss agent while avoiding the usual detrimental factors, unwanted effects, and adverse toxic or psychological effects which are associated with the racemic mixture of fluoxetine. In addition, these compositions possess potent activity in the treatment of migraine headaches, pain, and obsessive-compulsive disorders, while avoiding the usual detrimental factors, unwanted effects and adverse toxic or psychological effects associated with the racemic mixture of fluoxetine. Also disclosed are methods of using these novel compositions of matter to treat migraine headaches, pain, obsessive-compulsive disorders and obesity or weight gain in a human by administering pure S(+) fluoxetine. These methods also avoid the usual detrimental factors, unwanted effects, and adverse toxic or psychological effects associated with administration of the racemic mixture of fluoxetine.

The active compound of this composition and method is an optical isomer of the compound fluoxetine which is described in U.S. Pat. Nos. 4,018,895 and 4,194,009 to Molloy, et al. Chemically, this isomer is (+)N-methyl-3-phenyl-3-[($\alpha,\alpha,\alpha$-trifluoro-p-tolyl)oxy]-propylamine, herein after referred to as S(+) fluoxetine.

BACKGROUND OF THE INVENTION

Many organic compounds exist in optically active forms, i.e., they have the ability to rotate the plane of plane-polarized light. In describing an optically active compound, the prefixes D and L or R and S are used to denote the absolute configuration of the molecule about its chiral center(s). The prefixes (+) and (−) or d and l are employed to designate the sign of rotation of plane-polarized light by the compound, with (−) or l meaning that the compound is levorotatory. A compound prefixed with (+) or d is dextrorotatory. For a given chemical structure, these compounds, called stereoisomers, are identical except that they are mirror images of one another. A specific stereoisomer may also be referred to as an enantiomer, and a mixture of such isomers is often called an enantiomeric or racemic mixture.

Stereochemical purity is of importance in the field of pharmaceuticals, where 12 of the 20 most prescribed drugs exhibit chirality. A case in point is provided by the L-form of propranolol, which is known to be 100 times more potent than the D-enantiomer.

Furthermore, optical purity is important since certain isomers may actually be deleterious rather than simply inert. For example, the D-enantiomer of thalidomide was a safe and effective sedative when prescribed for the control of morning sickness during pregnancy. However, its L-thalidomide counterpart was discovered to be a potent teratogen.

Fluoxetine (Prozac®), which is the subject of the present invention, is available only as a racemic mixture. That is, it is a mixture of optical isomers, called enantiomers.

The racemic mixture of fluoxetine, in addition to its use as an antidepressant, has a wide spectrum of actual and potential activities which include:
Treatment of diabetes (EPA 88303930.7)
Assisting in weight loss—i.e., appetite suppression (U.S. Pat. No. 4,895,845)
Treatment of alcohol abuse (U.S. Pat. No. 4,777,173)
Analgesia—control of pain (U.S. Pat. Nos. 4,698,342 and 4,594,358)
Treatment of atherosclerosis (U.S. Pat. No. 4,444,778)
Improvement of memory (U.S. Pat. No. 4,647,591)
Treatment of anxiety (U.S. Pat. No. 4,590,213)
Treatment of hypertension (U.S. Pat. No. 4,329,356)
Treatment of Huntington's chorea and schizophrenia (Scrip's New Product Review No.7, "Fluoxetine", PJB Publications Ltd. 1986)

Whereas the foregoing Molloy et al. patents, in addition to the above discussed European patent application and U.S. patents, recognize that compounds such as fluoxetine have optically active forms, no example of an optically active form is given. Furthermore, prior art studies with the enantiomers of fluoxetine have generally concluded that the fluoxetine enantiomers are equipotent and that there is no advantage in the use of the pure S-enantiomer. See, Robertson et al., *J. Med. Chem.*, 31: 1412–1417 (1988). However, it has now been discovered that there are indeed unforeseen advantages in the use of the pure S-enantiomer of fluoxetine.

Various researchers have presented a limited amount of pharmacological data on the enantiomers of fluoxetine. See, Fuller et al., *Pharm. Biochem. Behav.*, Vol. 24 pg. 281–284 (1986); Robertson et al., *J. Med. Chem.*, Vol. 31 pg. 1412–1417 (1988); Wong et al. *Drug Devel. Res.* Vol. 6 pg. 397–403 (1985); Wong et al., *Pharm. Biochem. Behav.*, Vol. 31 pg. 475–479 (1988). These references are limited by their failure to provide complete dose-response or pharmacokinetic analyses, resulting only in qualitative impressions on certain matters.

The primary use of fluoxetine is in the treatment of depression, which along with mania falls under the heading of affective disorders. Mania and depression are characterized by changes in mood as the primary symptom. Either of these two extremes of mood may be accompanied by psychosis with disordered thought and delusional perceptions. Psychosis may have, as a secondary symptom, a change in mood, and it is this overlap with depression that causes much confusion in diagnosis. Severe mood changes without psychosis frequently occur in depression and are often accompanied by anxiety. Depression is characterized by feelings of intense sadness or pessimistic worry, agitation, self-deprecation, physical changes (including insomnia, anorexia, and loss of drive, enthusiasm, and libido), and mental slowing. Among the more common treatments for depression are the administration of a tricyclic antidepressant agent.

Fluoxetine is not in the class of drugs known as tricyclic antidepressants. Its antidepressant action is presumed to be based on its highly specific inhibition of serotonin uptake in serotonergic neurons and platelets in the brain. It is also chemically unrelated to tetracyclic or other available antidepressant agents.

Fluoxetine can also be used to assist in weight loss as disclosed in U.S. Pat. No. 4,895,845 to Seed. The causes of excess body weight and/or obesity are complex; however, a common denominator in the overweight person's diet is a caloric intake which exceeds that person's body expenditures. One method of treating a person who is overweight and/or obese is to restrict that person's caloric intake, in combination with an exercise regimen. This method may be limited in its effectiveness since many overweight or obese people have developed eating and activity patterns which are counterproductive to achieving weight reduction. Another method to treat overweight or obese patients is to administer appetite suppressant drugs in conjunction with a weight reduction program. The drawback to this method is that many appetite suppressant drugs produce unwanted or adverse effects which limit their usefulness such as long duration of action which results in severe appetite suppression.

It has also been suggested that fluoxetine could be used to treat migraine headaches which are a paroxysmal disorder characterized by recurrent attacks of said headaches, with or without associated visual and gastrointestinal disturbances. The cause is unknown, but evidence suggests a genetically transmitted functional disturbance of cranial circulation. Prodromal symptoms may be due to intracerebral vasoconstriction, and the head pain to dilation of scalp arteries. Migraine may occur at any age but usually beings between ages 10 and 30, more often in women than in men. Migraine headaches may be preceded by a short period of depression, irritability, restlessness or anorexia, and in some patients by scintillating scotomas, visual field defects, paresthesias, or (rarely) hemiparesis. These symptoms may disappear shortly before the headache appears or may merge with it. Pain is either unilateral or generalized. Symptoms usually follow a pattern in each patient, except that unilateral headaches may not always be on the same side. The patient may have attacks daily or only once in several months.

Furthermore, it has also been suggested that fluoxetine could be used to treat pain, in particular chronic pain. Pain is a complex subjective phenomenon comprised of a sensation indicating real or potential tissue damage and the affective response this generates. Pain can be classified as either acute or chronic pain. Acute pain is an essential biologic signal of the potential for or the extent of injury. It is usually short-lived and is associated with hyperactivity of the sympathetic nervous system; e.g., tachycardia, increased respiratory rate and blood pressure, diaphoresis, and pupillary dilation. The concurrent affect is anxiety. Treatment involves removal of the underlying etiology if possible and the use of analgesic drugs. Chronic pain is defined as pain persisting for greater than six months. Pain of this duration loses its adaptive biologic role. Vegetative signs gradually develop; e.g., lassitude, sleep disturbance, decreased appetite, loss of taste for food, weight loss, diminished libido, and constipation. A depressed affect predominates. In many patients, organic disease may be insufficient to explain the degree of pain or may be altogether absent. In these patients, as well as in many with organic disease, the psychologic factors become the primary contributor to impairment. Therapy is often difficult and prognosis is guarded.

In addition, it has been postulated that fluoxetine is effective in the treatment of obsessive-compulsive disorders. This is a neurotic disorder characterized by the presence of recurrent ideas and fantasies (obsessions) and repetitive impulses or actions (compulsions) that the patient recognizes as morbid and toward which he feels a strong inner resistance. Anxiety is a central feature, but in contrast to the phobias (where the patient is anxious in the face of external dangers of which he perceives himself to be the passive victim), the anxiety arises in response to internally derived thoughts and urges that the patient fears he may actively carry out despite his wishes not to. Obsessive-compulsive patients comprise less than 5% of those with neurotic disorders, and about 0.05% of the population at large. The neurosis affects men and women equally and tends to be found in individuals from upper socioeconomic levels and with higher intelligence.

Fluoxetine has been shown to have certain advantages over other antidepressant drugs. Antagonism of muscarinic, histaminergic and $\alpha_1$ adrenergic receptors has been hypothesized to be associated with various anticholinergic and cardiovascular effects of classical tricyclic antidepressant drugs. Fluoxetine binds to these and other membrane receptors from brain tissue much less potently than do these tricyclic antidepressants. Thus, fluoxetine gives less anticholinergic side effects such as blurred vision, dry mouth, constipation and urinary retention. There is also less lowering of blood pressure, tachycardia and arrhythmias.

While fluoxetine has certain advantages, it also has disadvantages. Among these disadvantages are side effects which include unwanted effects and adverse toxic or psychological effects. The most frequently reported side effects associated with racemic fluoxetine are headaches, nervousness, anxiety and insomnia. These are reported by 10% to 15% of patients treated with fluoxetine. These symptoms led to drug discontinuation in 5% of the patients treated with the drug. It is also known that in some patients, use of fluoxetine is associated with severe anxiety leading to intense violent suicidal thoughts and self mutilation. Teicher et al., *Am. J. Psychiatry*, 147(2): 207–210 (1990). In other patients manic behavior follows treatment with fluoxetine. Other side effects associated with fluoxetine include nausea, nervousness, tremor, fatigue, mouth dryness, dyspepsia, constipation, excessive sweating, upper respiratory infection, flu-like syndrome, diarrhea and drowsiness.

Another disadvantage of racemic fluoxetine is its long half-life and the concomitant delay in onset of action. The half-life of racemic fluoxetine is approximately 2 to 3 days. Steady state plasma concentrations are achieved only after continuous dosing for weeks.

A further disadvantage of racemic fluoxetine is that it has a low response rate. Overall, 44% of the patients being treated with fluoxetine showed antidepressant effect. In patients who had not previously responded to other antidepressant therapy the response to fluoxetine was 43%. In addition, in patients with no previous treatment with antidepressants, or with a history of good response to previous treatment, response to fluoxetine was 56%. (*Scrip's New Product Review*, "No. 7 Fluoxetine", pages 13–14, 1986).

Another disadvantage of racemic fluoxetine is that in addition to its use as an antidepressant it has activities such as severe appetite suppression, drowsiness, analgesia and hypotension. These other activities may be unwanted effects when treating a patient suffering from depression or even when treating obesity or weight gain, i.e., where only moderate appetite suppression of short duration is desired.

Racemic fluoxetine has been alleged to have adverse side effects or unwanted effects on sexual function when it is used as an antidepressant in certain patients. See, e.g., Kline, M.D., *American Journal of Psychiatry*, 146, 804–805 (1989); Lydiard, R. B. & George, M. S., *South African Medical Journal*, 82, 933–934 (1989). However, there has been a suggestion that there may be beneficial effects on sexual dysfunction associated with the use of racemic fluoxetine as an antidepressant. Power-Smith (1994), *British Journal of Psychiatry*, 164, 249–250. These beneficial effects on sexual dysfunction are believed to be associated with the activity of racemic fluoxetine as a serotonin reuptake blocker.

It is therefore desirable to find a compound with the advantages of fluoxetine which would not have the above described disadvantages.

SUMMARY OF THE INVENTION

It has now been discovered that the S(+) isomer of fluoxetine does not have certain side effects, including causing nervousness, anxiety, insomnia, and adverse psychological effects; has a fast onset of action and an increased response rate. It has also been discovered that with the use of the S(+) isomer of fluoxetine it is possible to avoid other activities of the racemic compound which would be unwanted effects when treating a patient suffering from depression. Thus, the S(+) isomer of fluoxetine is useful for methods of treating depression and in the compositions used thereof where these detrimental effects will be avoided.

It has also been discovered that with the use of the S(+) isomer of fluoxetine it is possible to achieve weight reduction or weight loss through moderate appetite suppression while avoiding unwanted effects, such as severe appetite suppression, and adverse toxic or psychological effects associated with administration of the racemic mixture of fluoxetine. Also, the methods and compositions of the present invention utilizing optically pure S(+) fluoxetine provide an increased response rate.

In addition, it has been discovered that the S(+) isomer of fluoxetine is useful in the treatment of migraine headaches, the treatment of pain, in particular chronic pain, and in the treatment of obsessive-compulsive disorders. It has been discovered that the S(+) isomer of fluoxetine is useful in the treatment of conditions alleviated or be improved by inhibition of serotonin uptake including but not limited to alcohol abuse, anxiety, memory disorders, sexual dysfunction, Huntington's chorea and schizophrenia. The unwanted effects and adverse toxic or psychological effects which are avoided or decreased by administering the S(+) isomer of fluoxetine include but are not limited to headaches, nervousness, anxiety, nausea, diarrhea, anorexia, insomnia, severe appetite suppression, inner restlessness (akathisia) suicidal thoughts and self mutilation.

Novel compositions of matter containing optically pure S(+) fluoxetine which have appetite suppressant activity while avoiding the above described unwanted effects and adverse toxic or psychological effects associated with the racemic mixture of fluoxetine are also disclosed.

Further included within the present invention are novel compositions of matter containing optically pure S(+) fluoxetine which are useful in the treatment of migraine headaches, the treatment of pain, in particular chronic pain, and the treatment of obsessive-compulsive disorders. These novel compositions also avoid the above-described unwanted, adverse toxic or psychological effects associated with the racemic mixture of fluoxetine.

DETAILED DESCRIPTION OF THE INVENTION

The present invention encompasses a method of eliciting an antidepressant effect while avoiding the concomitant liability of adverse toxic or psychological effects, delayed onset of action or low response rate associated with the racemic mixture which comprises administering to a patient in need of antidepressant therapy an amount sufficient to alleviate human depression, but insufficient to cause said adverse toxic or psychological effects, delayed onset of action and low response rate, of S(+) fluoxetine or a pharmaceutically acceptable salt thereof, substantially free of its R(−) stereoisomer.

The present invention also encompasses a method of treating obesity or weight gain in a human while avoiding unwanted effects, adverse toxic or psychological effects or low response rate associated with the racemic mixture of fluoxetine, comprising administering to a human in need of treatment of obesity or weight gain an amount of S(+) fluoxetine or a pharmaceutically acceptable salt thereof, substantially free of its R(−) stereoisomer, said amount being sufficient to alleviate said human's obesity or weight gain but insufficient to cause said unwanted effects and adverse toxic or psychological effects associated with administration of racemic fluoxetine.

In addition, the present invention encompasses a method of treating migraine headaches, pain or obsessive-compulsive disorders while avoiding concomitant liability of unwanted effects, adverse toxic or psychological effects or low response rate associated with the racemic mixture of fluoxetine, comprising administering to a patient in need of treatment of migraine headaches, treatment of pain or treatment of obsessive-compulsive disorders, an amount of S(+) fluoxetine or a pharmaceutically acceptable salt thereof, substantially free of its R(−) stereoisomer, said amount being sufficient to treat the patient's migraine headache, pain or obsessive-compulsive disorders but insufficient to cause said unwanted effects, adverse toxic or psychological effects or low response rate associated with administration of racemic fluoxetine.

The present invention further encompasses a method of eliciting an antidepressant effect while avoiding unwanted effects, which comprises administering to a patient in need of antidepressant therapy an amount sufficient to alleviate a human's depression, but insufficient to cause said unwanted effects of S(+) fluoxetine or a pharmaceutically acceptable salt thereof, substantially free of its R(−) stereoisomer.

The present invention also encompasses an antidepressant composition for the treatment of a patient in need of antidepressant therapy which comprises an amount sufficient to alleviate the depression but insufficient to cause adverse toxic or psychological effects, delayed onset of action and low response rate of S(+) fluoxetine or a pharmaceutically acceptable salt thereof, substantially free of its R(−) stereoisomer.

Also embodied in the present invention is an antidepressant composition adapted for the treatment of a patient in need of antidepressant therapy which comprises an amount sufficient to alleviate the depression but insufficient to cause the unwanted effects of S(+) fluoxetine or a pharmaceutically acceptable salt thereof, substantially free of its R(−) stereoisomer.

Further, embodied in the present invention is a composition that is useful for treating obesity or weight gain in a human comprising an amount of S(+) fluoxetine or a pharmaceutically acceptable salt thereof, substantially free of its R(−) stereoisomer, said amount being sufficient to achieve weight loss or prevent weight gain while avoiding unwanted effects, adverse toxic or psychological effects or low response rate associated with the racemic mixture of fluoxetine.

In addition, the present invention encompasses compositions that are adapted for treating migraine headaches, pain, or obsessive-compulsive disorders, comprising an amount of S(+) fluoxetine or a pharmaceutically acceptable salt thereof, substantially free of its R(−) stereoisomer, said amount being sufficient to alleviate the above-described afflictions, but insufficient to cause unwanted effects, adverse toxic or psychological effects or low response rate of racemic fluoxetine.

Furthermore, pure S(+) fluoxetine is also more effective for the treatment of migraine headaches, the treatment of pain, in particular chronic pain, and to treat obsessive-compulsive disorders, since as previously discussed the racemic mixture of fluoxetine has a delayed onset of action, and has a low response rate whereas S(+) isomer of fluoxetine does not cause unwanted effects or adverse toxic or psychological effects and it has a high response rate. Thus, it is more desirable to use the S(+) isomer of fluoxetine. With regard to migraine headaches in particular, the reductions of adverse toxic or psychological effects by the S(+) isomer of fluoxetine allows for treatment of the symptoms on an acute basis and also prophylactically, without the previously described adverse effects or complications.

In addition, the present invention encompasses a method for treating a condition alleviated or improved by inhibition of serotonin uptake in serotonergic neurons and platelets in a human while avoiding unwanted, adverse toxic or psychological effects associated with the racemic mixture of fluoxetine which comprises administering to a human in need of such therapy an amount of S(+) fluoxetine or a pharmaceutically acceptable salt thereof, substantially free of its R(−) stereoisomer, said amount being sufficient to alleviate said condition but insufficient to cause said adverse effects. Conditions that may be alleviated or improved by inhibition of serotonin uptake in serotonergic neurons and platelets include but are not limited to alcohol abuse, anxiety, memory disorders, sexual dysfunction, Huntington's chorea and schizophrenia.

Further encompassed in the present invention is a composition for the treatment of a condition alleviated or improved by inhibition of serotonin uptake in serotonergic neurons and platelets in a human which comprises an amount of S(+) fluoxetine or a pharmaceutically acceptable salt thereof, substantially free of its R(−) stereoisomer, said amount being sufficient to alleviate said condition but insufficient to cause unwanted, adverse toxic or psychological effects associated with the administration of racemic fluoxetine.

The racemic mixture of fluoxetine (i.e., a mixture of R and S stereoisomers) has antidepressant effect; however this racemic mixture causes adverse toxic or psychological effects, has a delayed onset of action, and has a low response rate. The S(+) isomer of fluoxetine does not cause these adverse toxic or psychological effects, has a rapid onset of action and has a high response rate. Thus, it is much more desirable to use the S(+) isomer of fluoxetine.

Furthermore, although there is some variability from one patient to another, it is generally observed that, by administering an effective amount of only the S(+) isomer of fluoxetine it is possible to accomplished a more "targeted" therapy. A more "targeted" therapy means that by using the S(+) isomer of fluoxetine the compound's broad activity can be taken advantage of without also having unwanted effects. This is important since it is not desirable for all patients to be administered a compound with such a complex and multifaceted spectrum of activity. The term "unwanted effects" includes but is not limited to (1) severe appetite suppression; (2) drowsiness or analgesia; and (3) hypotension. Thus, by administering to a patient the S(+) isomer of fluoxetine, significant antidepressant activity is obtained without the above-identified unwanted effects which are associated with the racemic mixture of fluoxetine.

The term "adverse toxic or psychological effects" includes but is not limited to headaches, nervousness, anxiety, insomnia, nausea, diarrhea, drowsiness, mouth dryness, tremor, anorexia, dyspepsia, excessive sweating, upper respiratory infection, flu-like syndrome, intense violent suicidal thoughts and manic behavior.

The term "side effect" as used herein means effects which are undesirable or which act against the intended beneficial effect of the compositions. The term "side effect" encompasses adverse toxic or adverse psychological effects.

The term "substantially free of the R(−) stereoisomer" as used herein means that the composition contains a greater proportion of the S(+) isomer of fluoxetine in relation to the R(−) isomer of fluoxetine. In a preferred embodiment the term "substantially free of its R(−) isomer" as used herein means that the composition contains at least 90% by weight of S(+) fluoxetine and 10% by weight or less of R(−) fluoxetine, these percentages being based on the total amount of fluoxetine present. In the most preferred embodiment the term "substantially free of the R(−) stereoisomer" means that the composition contains at least 99% by weight S(+) fluoxetine and 1% or less of R(−) fluoxetine. In another preferred embodiment, the term "substantially free of its R(−) stereoisomer" as used herein means that the composition contains 100% by weight of S(+) fluoxetine. Again, the above percentages are based on the total amount of fluoxetine present. The terms "substantially optically pure S(+) fluoxetine" and "optically pure S(+) isomer of fluoxetine" are also encompassed by the above-described amounts.

The term "eliciting an antidepressant effect" means relief from the symptoms associated with depression, which include but are not limited to feelings of intense sadness or pessimistic worry, agitation, self-deprecation, physical changes (including insomnia, anorexia, and loss of drive enthusiasm and libido) and mental slowing.

The term a "method of treating migraine headaches, pain or obsessive-compulsive disorders" as used herein means relief from the symptoms and/or effects associated with these disorders that are described above.

The term a "method of treating obesity or weight gain" as used herein means a method of non-severely suppressing the appetite of a human for a short time such that food consumption is reduced by the non-severe appetite suppression.

The term a "method for treating a condition alleviated or improved by inhibition of serotonin uptake in serotonergic neurons and platelets" as used herein means relief from the symptoms and/or effects associated with these disorders.

The term "sexual dysfunction" as used herein includes, but is not limited to, erectile impotence and/or premature ejaculation. Thus, the term "method of treating sexual dysfunction" as used herein means a method of eliciting advantageous effects on human sexual function, in particular, the treatment or prevention of erectile impotence and/or premature ejaculation in males. S(+) fluoxetine can be used to treat sexual dysfunction in patients in need thereof or to prevent sexual dysfunction in humans associated with depression or aging. S(+) fluoxetine can achieve these desired effects on sexual function while reducing unwanted, adverse toxic or psychological effects associated with the administration of racemic fluoxetine. The dosage and the dosage schedule for use of S(+) fluoxetine in the treatment or prevention of sexual dysfunction is as described below.

The synthesis of the S(+) isomer of fluoxetine can be performed by two methods which are as follows:

Method 1

This method is disclosed in Gao, et al. *J. Org. Chem.* Vol. 53, No. 17, pp. 4081–4084 (1988). It involves the use of 1-phenyl-1,3-propanediols, which are key intermediates. The 1-phenyl-1,3-propanediols are prepared from cinnamyl epoxy alcohols by Red-Al® reduction. The chiral cinnamyl epoxy alcohols are made by asymmetric epoxidation of cinnamyl alcohols as disclosed in Gao, et al.

(S)-(+)-fluoxetine hydrochloride is prepared from (2R, 3R)-epoxycinnamyl alcohol obtained by the asymmetric epoxidation disclosed in Gao et al. utilizing (−)-DIPT.

The reaction is scheme as follows:

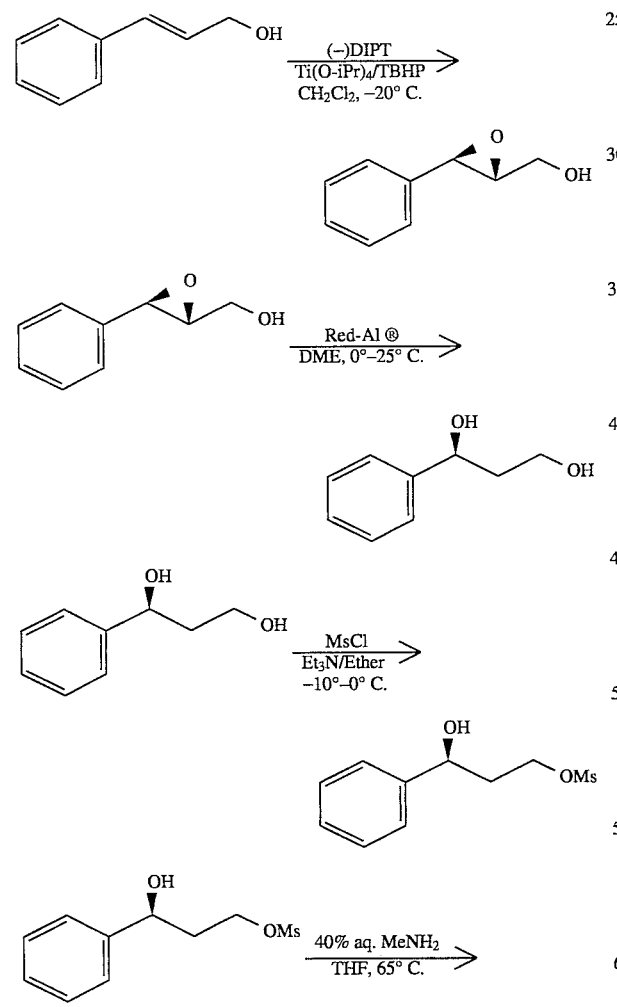

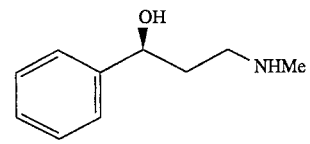

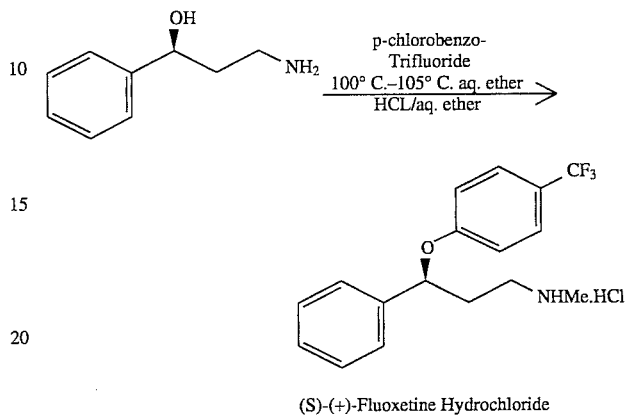

(R)-(−)-fluoxetine hydrochloride is prepared from (2S, 3S)-epoxycinnamyl alcohol obtained by the asymmetric epoxidation disclosed in Gao et al. utilizing (+)-DIPT.

Method 2

This method is based on the asymmetric reduction of ketone with a chiral borane reagent as disclosed in U.S. Pat. No. 4,868,344 to H. C. Brown.

The reaction scheme is as follows:

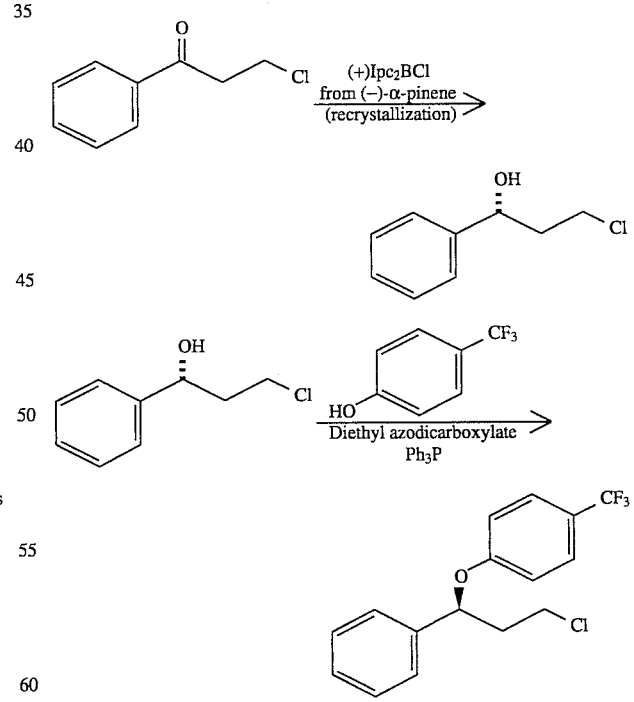

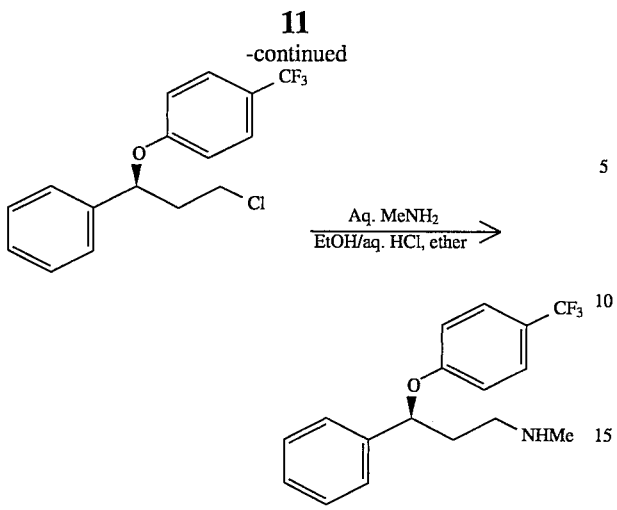

The magnitude of a prophylactic or therapeutic dose of S(+) fluoxetine will, of course, vary with the nature and the severity of the condition to be treated and its route of administration. It will also vary according to the age, weight and response of the individual patient. In general, the daily dose range for the use of S(+) fluoxetine to treat or prevent the disorders described herein will lie within the range of from about 1 mg to about 100 mg per day, preferably about 20 mg to about 80 mg per day, and most preferably from about 40 mg to about 80 mg per day, in single or divided doses. On the other hand, it may be necessary to use dosages outside these limits in some cases. The terms encompassed by the above-described amounts include: "a therapeutically effective amount", "an amount sufficient to alleviate said human's depression but insufficient to cause said adverse toxic or psychological effects, delayed onset of action or low response rate", "said amount being sufficient to alleviate migraine headaches, pain or an obsessive-compulsive disorder but insufficient to cause unwanted, adverse toxic or psychological effects", "said amount being sufficient to alleviate said human's obesity or weight gain but insufficient to cause said unwanted, adverse toxic or psychological effects", "said amount being sufficient to achieve weight loss but insufficient to cause said unwanted, adverse toxic or psychological effects", "said amount being sufficient to alleviate said condition but insufficient to cause said unwanted, adverse toxic or psychological effects" wherein said condition is alcohol abuse, anxiety, sexual dysfunction, memory disorders, Huntington's chorea or schizophrenia.

Any suitable route of administration may be employed for providing the patient with an effective dosage of S(+) fluoxetine. For example, oral, rectal, parenteral, transdermal, subcutaneous, intramuscular, inhalation and the like may be employed. Dosage forms include tablets, trochees, dispersions, suspensions, solutions, capsules, patches and the like.

The pharmaceutical compositions of the present invention comprise S(+) fluoxetine as an active ingredient or a pharmaceutically acceptable salt thereof, and may also contain a pharmaceutically acceptable carrier and optionally other therapeutic ingredients. The term "pharmaceutically acceptable salts" refers to salts prepared from pharmaceutically acceptable non-toxic acids including inorganic acids and organic acids.

Since the compound of the present invention is basic, salts may be prepared from pharmaceutically acceptable non-toxic acids, including inorganic and organic acids. Such acids include acetic, benzenesulfonic, benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic and the like. Particularly preferred are hydrobromic, hydrochloric, phosphoric and sulfuric acids.

The compositions include compositions suitable for oral, rectal, and parenteral (including subcutaneous, intramuscular, and intravenous) administration, although the most suitable route in any given case will depend on the nature and severity of the condition being treated. The most preferred route of administration in the present invention is oral. The compositions may be inconveniently presented in unit dosage form and prepared by any of the methods well-known in the art of pharmacy.

In the case where an oral composition is employed, a suitable dosage range for use is, e.g., from about 1 mg to about 100 mg of fluoxetine per day, preferably from about 20 mg to about 80 mg per day and most preferably from about 40 mg to about 80 mg per day.

In practical use, S(+) fluoxetine can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). In preparing the compositions for oral dosage form, any of the usual pharmaceutical media may be employed, such as, for example, water, glycols, oils, alcohols, flavoring agents, preservatives, coloring agents and the like in the case of oral liquid preparations, such as, for example, suspensions, elixirs and solutions; or carriers such as starches, sugars, microcrystalline cellulose, diluents, granulating agents, lubricants, binders, disintegrating agents and the like in the case of oral solid preparations such as, for example, powders, capsules and tablets, with the solid oral preparations being preferred over the liquid preparations. The most preferred solid oral preparation is capsules. Because of their ease of administration, tablets and capsules represent the most advantageous oral dosage unit form, in which case solid pharmaceutical carriers are obviously employed. If desired, tablets may be coated by standard aqueous or nonaqueous techniques.

In addition to the common dosage forms set out above, the compound of the present invention may also be administered by controlled release means and/or delivery devices such as those described in U.S. Pat. Nos. 3,845,770; 3,916,899; 3,536,809; 3,598,123; 3,630,200 and 4,008,719, the disclosures of which are hereby incorporated herein by reference. The use of a racemic mixture of fluoxetine in a sustained release formulation is disclosed and/or claimed in U.S. Pat. Nos. 4,797,286 and 4,847,092.

Pharmaceutical compositions of the present invention suitable for oral administration may be presented as discrete units such as capsules, cachets or tablets each containing a predetermined amount of the active ingredient, as a powder or granules or as a solution or a suspension in an aqueous liquid, a nonaqueous liquid, an oil-in-water emulsion or a water-in-oil liquid emulsion. Such compositions may be prepared by any of the methods of pharmacy but all methods include the step of bringing into association the active ingredient with the carrier which constitutes one or more necessary ingredients. In general, the compositions are prepared by uniformly and intimately admixing the active ingredient with liquid carriers or finely divided solid carriers or both, and then, if necessary, shaping the product into the desired presentation. For example, a tablet may be prepared by compression or molding, optionally with one or more accessory ingredients. Compressed tablets may be prepared by compressing in a suitable machine, the active ingredient in a free-flowing form such as powder or granules, optionally mixed with a binder, lubricant, inert diluent, and/or surface active or dispersing agent. Molded tablets may be made by molding in a suitable machine, a mixture of the powdered compound moistened with an inert liquid diluent. Desirably, each tablet contains from about 5 mg to about 100 mg of the active ingredient and each cachet or capsule contains from about 5 to about 100 mg of the active ingredient. Most preferably the tablet, cachet or capsule contains 20 mg of active ingredient.

The invention is further defined by reference to the following examples describing in detail the preparation of the compound and compositions of the present invention. It will be apparent to those skilled in the art that many modifications, both to materials and methods, may be practiced without departing from the purpose and interest of this invention.

All temperatures are in degrees Celsius.

EXAMPLES

EXAMPLE 1

Synthesis of R(–) and S(+) Fluoxetine Reduction of Epoxycinnamyl Alcohols with Red-Al; Synthesis of Fluoxetine Part 1

(R)-3-Phenyl-1,3-dihydroxypropane

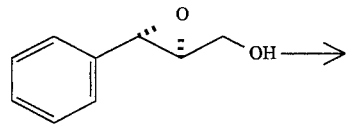

(1)

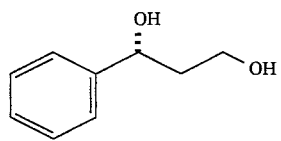

(2)

To a solution of (–)-(2S,3S)-epoxycinnamyl alcohol (1) (1.5 g, 10.0 mmol) (synthesized by the method disclosed in Gao et al., *J. Org. Chem.*, Vol. 53, No. 17, pp. 4081–4084 (1988).), in dimethoxyethane (50 mL) was added a 3.4 molar solution of Red-Al® in toluene (3.1 mL, 10.5 mmol) dropwise under nitrogen at 0° C. After stirring at room temperature for three hours, the solution was diluted with ether and quenched with 5% HCl solution. After stirring at room temperature for 30 min, the resulting white precipitate formed was filtered and boiled with ethyl acetate and filtered again. The combined organic solutions were dried with magnesium sulfate. Concentration gave (R)-3-phenyl-1,3-dihydroxypropane (2) as a slightly yellow oil which was used without further purification (1.5 g, 98%): ¹H NMR (CDCl₃) δ7.2–7.3 (m, 5 H), 4.88–4.98 (m, 1 H), 3.78–3.86(t, J=7.5 Hz, 2), 3.3–3.4 (br. s, 1 H), 2.85–2.95 (br. s, 1 H) , 1.84–2.08 (m, 2 H); the ratio of 1,3-diol to 1,2-diol was 20:1 by ¹H NMR analysis of the derived diacetate.

(S)-3-Phenyl-1,3-dihydroxypropane was prepared according to the above procedure starting with 300 mg of (+)-epoxycinnamyl alcohol to provide 300 mg of (S)-3-phenyl-1,3-dihydroxypropane (1,3-diol:1,2-diol=21:1).

Part 2

(S)-3-phenyl-3-hydroxypropyl-1-methanesulfonate

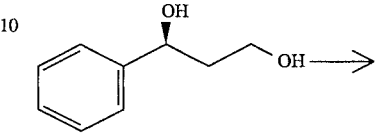

(3)

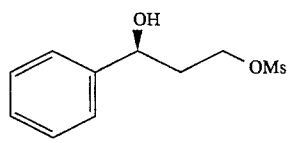

(4)

To a solution of (S)-3-phenyl-1,3-dihydroxypropane (3) (2.71 g, 17.8 mmol) and triethylamine (2.60 g, 25.6 mmol) in ether (90 mL) was added dropwise MsCl (1.45 mL, 18.7 mmol) under nitrogen at –10° C. After stirring at –10° C. to 0° C. for 3 h, the mixture was poured into ice water (30 mL) and washed with 20% H₂SO₄, saturated aqueous NaHCO₃, brine, and dried over magnesium sulfate. The crude products were purified by chromatography eluting with 45% ethyl acetate in hexane to give the title compound (4) as an oil (3.50 g, 85%): ¹H NMR (CDCl₃ δ7.3–7.4 (m, 5 H), 4.85–4.91 (t, J=7.7 Hz, 1 H), 4.42–4.52 (m, 1 H), 4.22–4.32 (m, 1 H), 3.0 (s, 3 H), 2.3 (s, 1 H), 2.1–2.2 (q, J=7.7 Hz, 2 H).

(R)-3-Phenyl-3-hydroxypropyl-1-methanesulfonate was prepared from (R)-3-phenyl-1,3-dihydroxypropane by the above procedure in 74% yield.

These two compounds were either stored at 0° C. or used soon after preparation.

Part 3

(S)-N-Methyl-3-phenyl-3-hydroxypropylamine

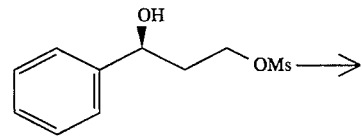

(5)

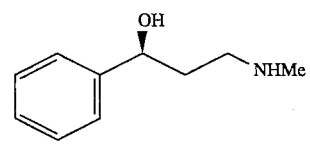

(6)

A solution of (S)-3-phenyl-3-hydroxypropyl-1-methanesulfonate (5) (690 mg, 3.0 mmol) and methylamine (10 mL, 40% in water) in THF (10 mL) was heated at 65° C. for 3 h. After cooling, the solution was diluted with ether and washed with saturated aqueous sodium bicarbonate, brine, and dried with anhydrous potassium carbonate. Concentration to dryness provided the title compound (6) (476 mg, 96%): $^1$H NMR (CDCl$_3$) δ7.2–7.4 (m, 5 H), 4.94 (dd, J=3.8, 7.2 Hz, 1 H), 3.4–3.9 (br. s, 1 H), 2.84–2.92 (m, 2 H), 2.45 (s, 3 H), 1.68–1.92 (m, 3 H).

Following a procedure identical to the above 1.15 g (R)-3-phenyl-3-hydroxypropyl-1-methanesulfonate yielded 837 mg of (R)-N-methyl-3-phenyl-3-hydroxypropylamine.

Part 4

(R)-Fluoxetine Hydrochloride

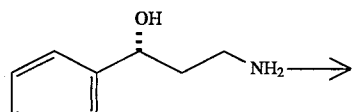

(7)

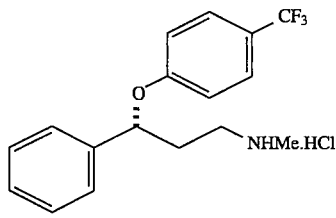

(8)

To a solution of (R)-N-methyl-3-phenyl-3-hydroxy-propylamine (7) (1.23 g, 7.45 mmol) in dimethyl acetamide (7 mL) was added sodium hydride (215 mg, 8.95 mmol) with cooling. The mixture was heated at 90° C. for 1.5 h, and an orange solution resulted. To this solution was then added 4-chlorobenzotrifluoride (3.23 g, 2.40 mL, 17.9 mmol), and the mixture was heated at 100°–105° C. for 2.5 h. After cooling and dilution with toluene, the mixture was washed with water, and the aqueous layer was separated and extracted with toluene. The combined toluene solutions were then washed with saturated aqueous sodium bicarbonate, brine, and dried over magnesium sulfate. Concentration provided (R)-fluoxetine as an orange oil (1.97 g, 86%). The oil was dissolved in ether and acidified with hydrogen chloride gas (pH=3–4) to give a acidic ethereal solution (no precipitate formed). The solution was concentrated at room temperature to give a yellow solid which was washed with ether to remove most of the orange color. The slightly yellow solid was then recrystallized from acetonitrile at −20° C. The solid was collected and washed with ether to provide (R)-fluoxetine hydrochloride (8) as a white powder (1.90 g, 75%): mp 140°–142° C. (lit. mp 140°–141.5° C.; [α]$^{23}$D −2.16° (c 1.62, MeOH); (lit.[α]$^{23}$D −1.97° [c 1.00, MeOH]); [α]$^{23}$D +7.08° (c 1.30, H$_2$O); (lit. [α]$^{23}$D +10.32° [c 1.00, H$_2$O]); IR (KBr, CDCl$_3$ 2950, 2640, 2450, 1620, 1595, 1520, 1360, 1250, 1180, 1170, 1130, 1114, 1070, 840 cm-1; $^1$H NMR (CDCl$_3$) δ9.72 (br, s, 2 H), 7.40–7.43 (d, J=8.7 Hz, 2 H), 7.25–7.33 (m, 5 H), 6.88–6.92 (d, J=8.7 Hz, 2 H), 5.45–5.50 (dd, J=4.6, 7.9 Hz, 1 H), 3.12 (br, s, 2 H), 2.55–2.62 (br, s, 3 H), 2.42–2.52 (m, 2 H); Anal. Calcd. for C$_{17}$H$_{19}$ClF$_3$NO: C, 59.05; H, 5.54; N, 4.05; F, 16.48; Cl, 10.25. Found: C, 58.84; H, 5.55; N, 3.94; F, 16.28; Cl, 10.50.

(S)-Fluoxetine hydrochloride was prepared by the above procedure from (S)-N-methyl-3-phenyl-3-hydroxypropylamine: mp 140°–142° C. (lit mp 135°–137° C.); [α]$^{23}$D −7.12° (c 1.53, H$_2$O); lit [α]$^{23}$D −10.85° [c 1.00, H$_2$O]); Anal. Calcd. for C$_{17}$H$_{19}$ClF$_3$NO: C, 59.05; H, 5.54; N, 4.05. Found: C, 59.19; H, 5.42; N, 3.89.

EXAMPLE 2

Oral Formulation

| Tablets: | | |
|---|---|---|
| | Quantity per Tablet (mg.) | |
| Formula | A | B |
| Active Ingredient (S(+) Flouxetine Hydrochloride) | 10.00 | 20.00 |
| Lactose | 62.75 | 52.75 |
| Corn Starch | 3.0 | 3.0 |
| Water (per thousand Tablets) | 30.0 ml | 30.0 ml* |
| Corn Starch | 18.75 | 18.75 |
| Magnesium Stearate | 0.5 | 0.5 |
| | 125.00 | 125.00 |

*The water evaporates during manufacture

Blend the active ingredient S(+) fluoxetine hydrochloride with the lactose until uniform. Blend the smaller quantity of cornstarch with the water and add the resulting corn starch paste, then mix until a uniform wet mass is formed. Add the remaining corn starch to the resulting wet mass and mix until uniform granules are obtained. Screen the granules through a suitable milling machine, using a ¼ inch stainless steel screen. Dry the milled granules in a suitable drying oven until the desired moisture content is obtained. Mill the dried granules through a suitable milling machine using ¼ mesh stainless steel screen. Blend in the magnesium stearate and compress the resulting mixture into tablets of desired shape, thickness, hardness and disintegration.

EXAMPLE 3

Oral Formulation

| Capsules: | | |
|---|---|---|
| | Quantity per Tablet (mg.) | |
| Formula | A | B |
| Active Ingredient | 10.00 | 20.00 |
| Lactose | 62.75 | 55.75 |
| Corn Starch | 18.75 | 18.75 |
| Magnesium Stearate | 0.50 | 0.50 |
| | 125.00 | 125.00 |

Blend the active ingredient, S(+) fluoxetine hydrochloride, lactose and corn starch until uniform; then blend the magnesium stearate into the resulting powder. Encapsulate the mixture into suitable sized two-piece hard gelatin capsules.

What is claimed is:

1. A method of treating migraine headaches in a human, comprising administering to said human a therapeutically effective amount of S(+) fluoxetine or a pharmaceutically acceptable salt thereof, substantially free of its R(−) stereoisomer.

2. The method of claim 1 wherein S(+) fluoxetine is administered by intravenous infusion, transdermal delivery, or orally as a tablet or a capsule.

3. The method of claim 1 wherein the amount administered is about 1 mg to about 100 mg per day.

4. The method according to claim 3 wherein the amount administered is about 20 mg to about 80 mg per day.

5. The method of claim 4 wherein the amount administered is from about 25 mg to about 75 mg per day.

6. The method of claim 1 wherein the amount of S(+) fluoxetine or a pharmaceutically acceptable salt thereof, is greater than approximately 90% by weight of the total amount of fluoxetine.

7. The method according to claim 1 wherein the amount of S(+) fluoxetine or a pharmaceutically acceptable salt thereof is greater than approximately 99% by weight of the total amount of fluoxetine.

8. The method according to claim 1 wherein S(+) fluoxetine or a pharmaceutically acceptable salt thereof, substantially free of its R(−) stereoisomer, is administered together with a pharmaceutically acceptable carrier.

9. A method according to claims 2, 3, 4 or 5 wherein S(+) fluoxetine is administered as its hydrochloride salt.

10. A method for preventing migraine headaches in a human patient in need thereof, which comprises administering to said human a therapeutically effective amount of S(+) fluoxetine or a pharmaceutically acceptable salt thereof, substantially free of its R(−) stereoisomer.

* * * * *